United States Patent
Blessing et al.

(10) Patent No.: US 8,180,603 B2
(45) Date of Patent: May 15, 2012

(54) PROCESS FOR PRODUCING SANDWICH STRUCTURES WITH PARTICULATE MATERIAL PATTERN

(75) Inventors: Horst Blessing, Euskirchen (DE); Hans-Adolf Jackels, Mechernich (DE)

(73) Assignee: The Procter & Gamble Company, Cincinnati, OH (US)

( * ) Notice: Subject to any disclaimer, the term of this patent is extended or adjusted under 35 U.S.C. 154(b) by 268 days.

(21) Appl. No.: 12/113,344

(22) Filed: May 1, 2008

(65) Prior Publication Data

US 2008/0215166 A1  Sep. 4, 2008

Related U.S. Application Data

(62) Division of application No. 11/192,149, filed on Jul. 28, 2005, now abandoned.

(30) Foreign Application Priority Data

Jul. 28, 2004 (EP) .................................... 04017789

(51) Int. Cl.
- G06F 7/60 (2006.01)
- G06F 17/10 (2006.01)
- G06F 17/50 (2006.01)

(52) U.S. Cl. ............................. 703/2; 703/1
(58) Field of Classification Search .............. 703/1, 2; 700/30, 31
See application file for complete search history.

(56) References Cited

U.S. PATENT DOCUMENTS

| | | |
|---|---|---|
| 3,860,003 A | 1/1975 | Buell |
| 4,381,783 A | 5/1983 | Elias |
| 4,610,678 A | 9/1986 | Weisman et al. |
| 4,741,941 A | 5/1988 | Englebert et al. |
| 4,800,102 A | 1/1989 | Takada |
| 4,834,735 A | 5/1989 | Alemany et al. |
| 4,888,231 A | 12/1989 | Angstadt |
| 4,994,053 A | 2/1991 | Lang et al. |
| 5,037,416 A | 8/1991 | Allen et al. |
| 5,151,092 A | 9/1992 | Buell et al. |
| 5,213,817 A | 5/1993 | Pelley |
| 5,260,345 A | 11/1993 | Desmarais et al. |
| 5,269,775 A | 12/1993 | Freeland et al. |

(Continued)

FOREIGN PATENT DOCUMENTS

EP  0 203 289 A2  12/1986

(Continued)

OTHER PUBLICATIONS

Dutkiewicz, Some advances in nonwoven structures for absorbency, comfort and aesthetics, Sep. 2002, AUTEX Research Journal, vol. 2, No. 3, pp. 153-165.*

(Continued)

*Primary Examiner* — Dwin M Craig
*Assistant Examiner* — Aniss Chad
(74) *Attorney, Agent, or Firm* — Laura L. Whitmer; Abbey A. Lopez

(57) ABSTRACT

The present invention is concerned with a process for forming a very well defined pattern of particulate material in a composite material comprising a web material and particulate absorbent material. The present invention relates also to a method for determining the equipment design and process parameter for such a process. In a particular application, the present invention provides a process for preparing liquid absorbent structures, such as may be useful for disposable absorbent articles.

7 Claims, 6 Drawing Sheets

U.S. PATENT DOCUMENTS

| | | | |
|---|---|---|---|
| 5,387,207 A | 2/1995 | Dyer et al. | |
| 5,397,316 A | 3/1995 | Lavon et al. | |
| 5,494,622 A | 2/1996 | Heath et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,625,222 A | 4/1997 | Yoneda et al. | |
| 5,662,758 A | 9/1997 | Hamilton et al. | |
| 5,925,439 A | 7/1999 | Haubach et al. | |
| 6,004,306 A | 12/1999 | Robles et al. | |
| 6,529,860 B1 | 3/2003 | Strumolo et al. | |
| 7,179,851 B2 * | 2/2007 | Qin et al. | 523/200 |
| 7,373,284 B2 * | 5/2008 | Stabelfeldt et al. | 703/2 |
| 7,634,394 B2 * | 12/2009 | Macura et al. | 703/6 |
| 2002/0095127 A1 | 7/2002 | Fish et al. | |
| 2002/0123848 A1 | 9/2002 | Schneiderman et al. | |
| 2003/0120234 A1 * | 6/2003 | Sorebo | 604/378 |
| 2003/0120249 A1 | 6/2003 | Wulz et al. | |
| 2004/0127131 A1 | 7/2004 | Potnis | |
| 2004/0236455 A1 | 11/2004 | Woltman et al. | |

FOREIGN PATENT DOCUMENTS

| | | |
|---|---|---|
| EP | 0752892 B1 | 7/2001 |
| EP | 1403419 A1 | 3/2004 |
| EP | 1447066 A1 | 8/2004 |
| FR | 2583377 A | 12/1986 |
| WO | WO 92/19198 A1 | 11/1992 |
| WO | WO 95/16746 A1 | 6/1995 |
| WO | WO 03/079946 A2 | 10/2003 |
| WO | WO 03/101622 A2 | 12/2003 |

OTHER PUBLICATIONS

White, Engineered structures for use in disposable incontinence products, Mar. 2003, Proc. Instn Mech. Engrs vol. 217 Part H: J. Engineering in Medicine, pp. 243-251.*

* cited by examiner

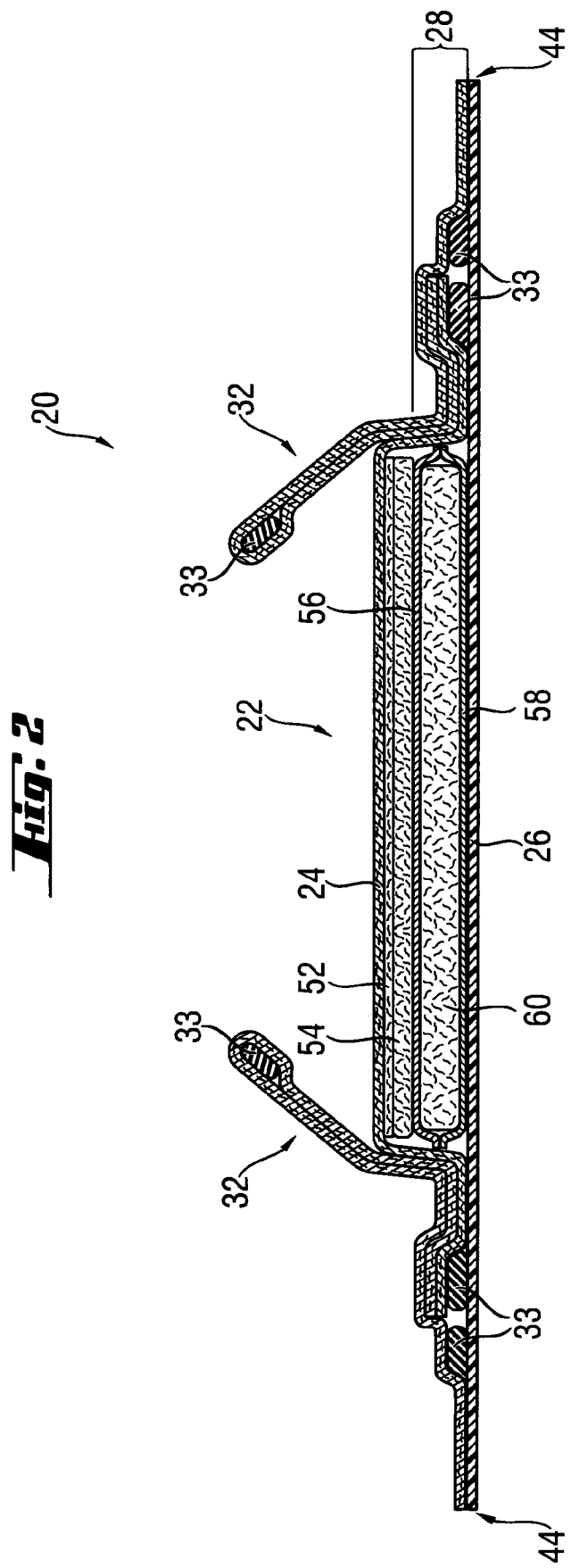

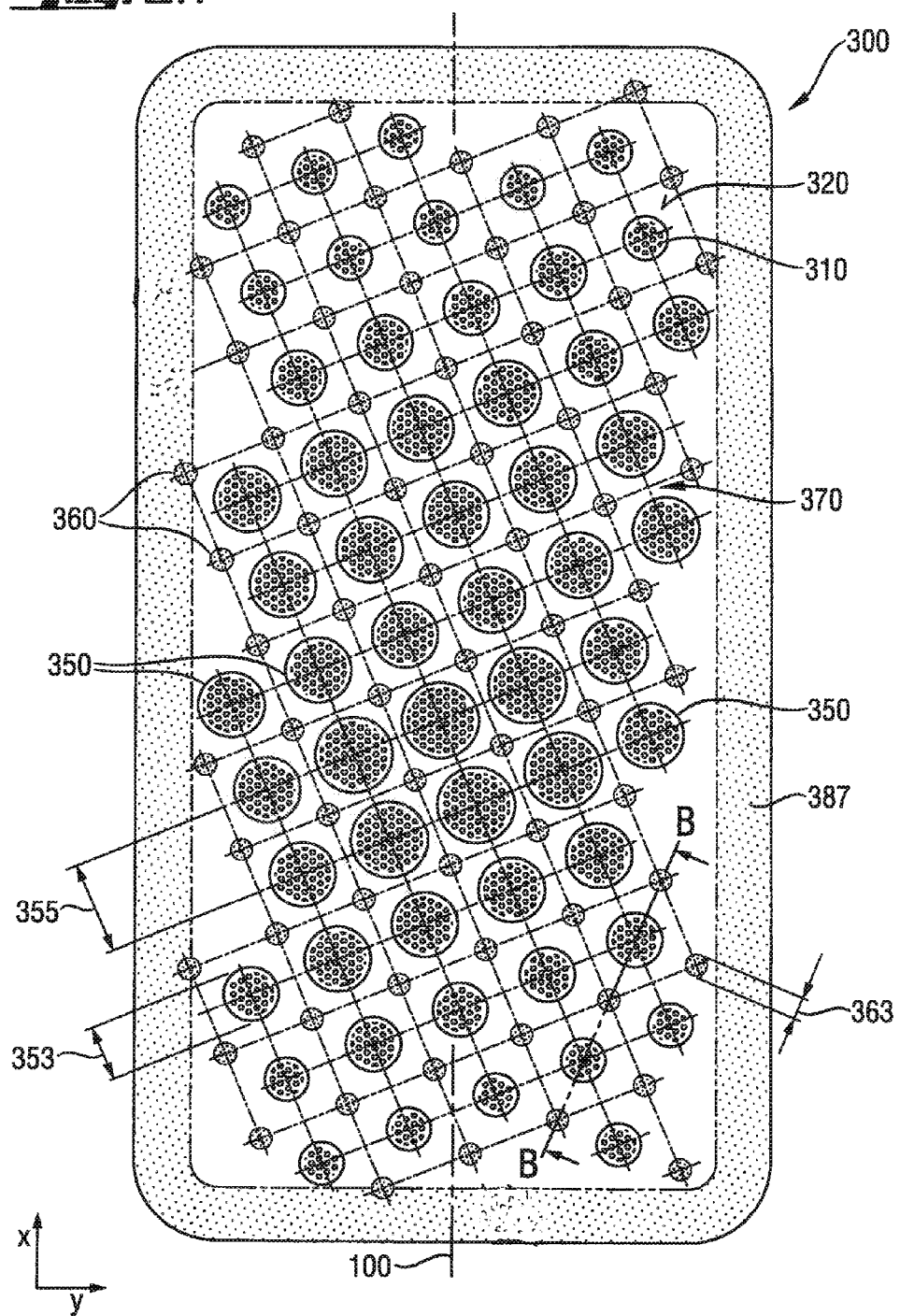

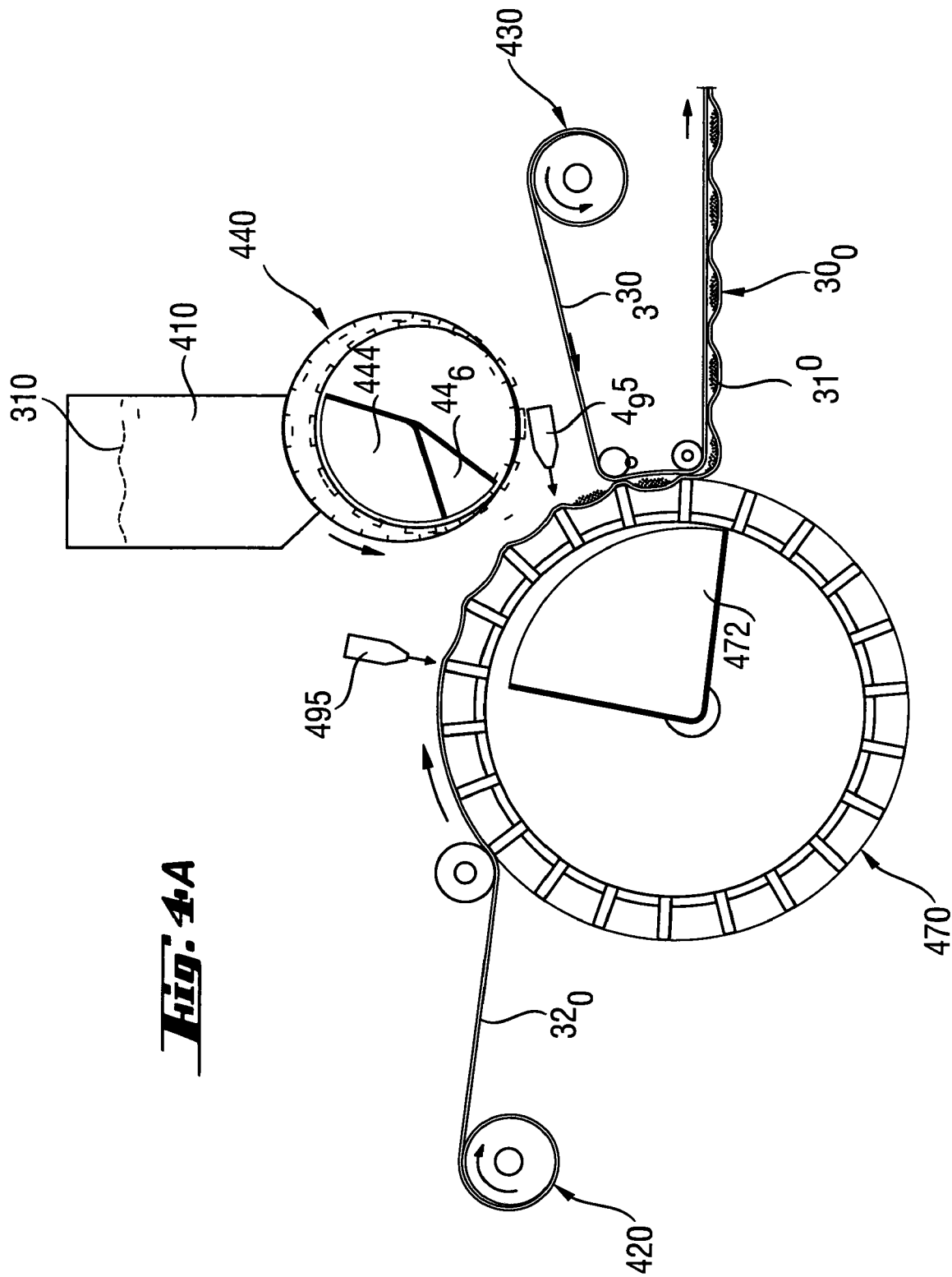

PROCESS FOR PRODUCING SANDWICH STRUCTURES WITH PARTICULATE MATERIAL PATTERN

CROSS REFERENCE TO RELATED APPLICATION

This application is a divisional of U.S. application Ser. No. 11/192,149, filed on Jul. 28, 2005 now abandoned.

FIELD OF THE INVENTION

The present invention is a process for forming a very well defined pattern of particulate material in a composite material comprising a web material and particulate absorbent material. The present invention relates also to a method for determining the equipment design and process parameter for such a process. In a particular application, the present invention provides a process for preparing liquid absorbent structures, such as may be useful for disposable absorbent articles.

BACKGROUND OF THE INVENTION

Composite structures comprising particulate material in a particular pattern are well known in the art, see, e.g. EP-A-1447066 (Busam et al.; P&G), disclosing an absorbent core for an absorbent article, which has a particulate absorbent material that is immobilized when wet. The absorbent core comprises a substrate layer an absorbent material, such as an absorbent polymer material.

U.S. Pat. No. 4,381,783 (Elias) discloses an absorbent article with a core comprising pockets of absorbent hydrocolloid material. These pockets are provided to confine the movement of absorbent polymer material, in particular when the article is fully or partially loaded with urine. The pockets form part of an absorbent layer and are typically provided from cellulose material. Hence, as to achieve good immobilization of the absorbent polymer material according to the teaching of this patent relatively high amount of cellulosic material is required. Moreover, the provision of such pockets may hinder the free distribution of liquid to the more absorbent areas of the core, for example the areas of the absorbent polymer materials.

Accordingly, processes to produce absorbent article having a non-homogeneous distribution of absorbent materials such as particulate absorbent polymer material, often referred to as absorbent gelling material or as super absorbents, are also known. In WO 03/101622A2 (Tombült et al.; P&G), a pulsing process for creating discontinuous particulate distribution is disclosed, and a similar structure may be produced according to U.S. Pat. No. 5,213,817 (Pelley; McNeill PPC).

Processes aiming at depositing a pattern of particulate absorbent material onto a web are described in U.S. Pat. No. 4,800,102 (Takada; Nordson), employing a rotating mask, or in WO 92/019198A (Perneborn/Mølnlycke) showing a linearly moving mask. FR-A-2583377 (Piron; Colgate Palmolive) discloses a metering drum into which absorbent powder is fed from a hopper for creating discontinuous pattern on a carrier on a conveyor belt. The drum is operated in a step-wise movement.

U.S. Pat. No. 5,494,622 (Heath et al.; K-C), aims at producing pockets of particles in a desired pattern on a web moving at high speed. A pattern chamber is supplied with particles of high absorbency material through which a gas permeable web is transported on a surface having a pattern of openings through which a vacuum is drawn so as to cause the particles to be deposited on the web in the pattern of the openings in the surface. The web carrying the particles is covered by a layer of liquid permeable material and the tension applied to the permeable web is varied to vary the porosity of the web. The particles are held on the web in the desired pattern of pockets while surplus particles between the pockets are removed. The thusly formed pockets form "islands", i.e. they are completely surrounded by bonded regions.

Whilst such documents describe various approaches to the deposition of particulate material onto a surface or on a moving substrate, there is still the need for a method to produce patterned particulate sandwiches in a very well defined pattern and at high production speeds. Further, whilst certain optimum conditions for each of these approaches may be read or deduced from the disclosures, there is no broadly applicable teaching as to how to arrive at the best suitable design with the best process settings, in particular for varying boundary conditions, like varying pattern, or lay-down basis weights, such as may be necessary for a complete product range.

Applying mathematical modeling simulations for analyzing processes and/or process parameter are known in the art, such as from U.S. Pat. No. 6,529,860 (Strumolo et al.; FORD). Therein, various computer related tools are employed to facilitate the design and testing of automotive vehicles, in particular with regard to investigate soil deposition on a vehicle panel.

However, so far no solution has been provided for the simulation of a particle lay-down system for forming particulate patterns, in particular not for application in the manufacturing of disposable absorbent articles.

SUMMARY OF THE INVENTION

Thus in one aspect, the present invention is a process of creating a sandwich structure comprising particulate material sandwiched between web materials in a very well defined pattern. This process comprises the steps of
creating such predetermined patterns in a pattern forming means on a transfer device,
depositing the thusly formed patterns on a carrier web material,
covering the pattern on this carrier material by a cover web material,
and bonding the carrier and cover web material to form the sandwich structure, thereby immobilizing the pattern.

To this end, there are provided: a particulate material; a transfer device comprising a first pattern forming means for receiving particulate material in a receiving region and transferring it to an discharging region, an essentially flat web material as carrier and/or cover material forming the outer layers of the sandwich; an essentially endless carrier support means for the carrier having a support pattern corresponding to the pattern of the first pattern forming means of the transfer device; a carrier material holding means for temporarily attaching the carrier material to the surface of the carrier support means; and sandwich fixation means for combining the sandwich structure The carrier and the cover material may be unitary for forming both outer sandwich layers or may be different materials forming the outer sandwich layers;

The process further comprises the execution of the following steps: transferring the particulate material to the receiving region of the transfer device, whereby the first pattern forming means defines a particulate cluster pattern; moving the pattern of particulate material to the discharging region of the transfer device; guiding the carrier web material over the carrier support means at a carrier speed corresponding to the carrier support speed; deforming the carrier web material by the carrier material holding means such that an indentation is formed in the unsupported regions, thereby forming a pattern corresponding to the particulate cluster pattern; expelling the particulate material from the transfer device towards the carrier; depositing the expelled particulate material on the deformed web carrier material; applying the cover material to the carrier material and the patterned particulate material, thereby forming a sandwich structure, providing fixation means for bonding the outer sandwich layers to each other at least in parts of the bonding area.

In a further aspect, the present invention is a method for determining the equipment design and process parameter for a process for selectively positioning particulate material onto a moving surface, by 1) providing a set of physical equations forming a physical model, the set of physical equations being connected by interaction boundary conditions,
   optionally comprising sub-models connected by sub-model connectivity boundary conditions,
2) selecting a set of fixed boundary conditions, comprising the overall equipment set-up, overall process requirements, and a set of (initial) operating conditions (fixed model input),
3) providing a set of predetermined model targets,
4) selecting a set of variable boundary conditions, which may vary throughout one simulation (variable model input),
5) performing calculus operations on the physical equations by using the fixed and variable model input,
6) transforming the calculus results into a model output, which is readable to a human analyst directly or preferably by a means of a computing device;
7) comparing the model output to predetermined model targets and determining the deviation there between,
8) modifying the set of variable boundary conditions, preferably by using computational equations for minimizing the deviation between the model output to predetermined model targets;
9) reiterating steps 4) to 8) until a preset exit criterion is met.

Preferably, these steps are performed by employing a computer device. The iterations may be terminated by defining a preset number of iterations of by defining a preset exit deviation criterion between the model output and the predetermined model targets.

In yet another aspect, the present invention is a system for determining the equipment design and process parameter for a process for selectively positioning particulate material onto a moving surface, the system comprising a memory device and a processor, disposed in communication with the memory device, the processor being configured a) to receive virtual simulation programs and overall boundary conditions;
b) simulation targets;
c) and simulation starting parameter so as to calculate a set of pre-defined output parameter and to transmit the output parameter to an output device.

BRIEF DESCRIPTION OF THE DRAWINGS

FIG. 2 shows a cross-sectional view of the disposable diaper of FIG. 1.

FIG. 3A shows a top view of an absorbent core sandwich structure.

FIG. 4A is a schematic process diagram for forming a sandwich structure.

DETAILED DESCRIPTION OF THE INVENTION

Figure 1:
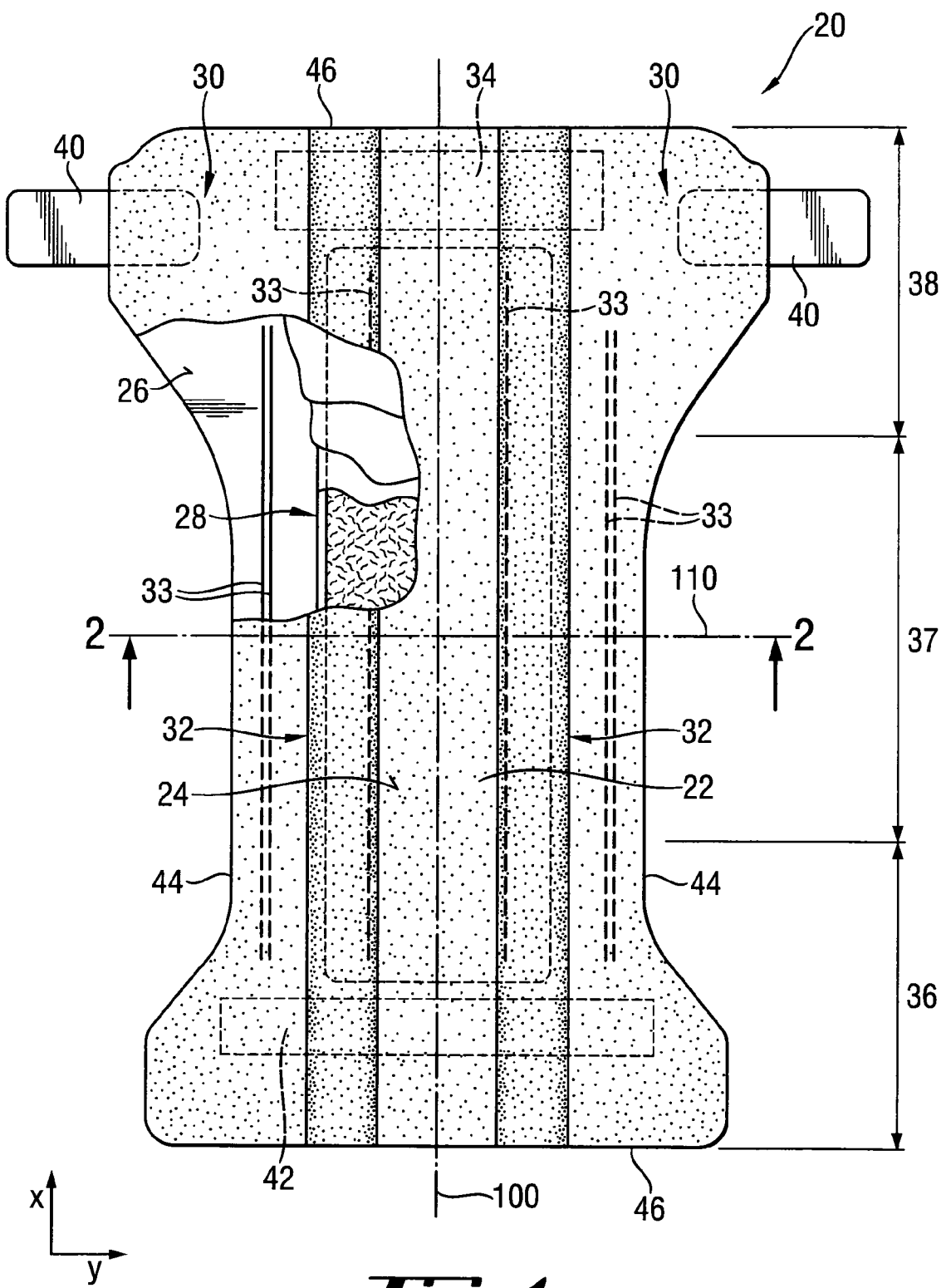
FIG. 1 is a top plan view of a disposable diaper, with the upper layers partially cut away.

As used herein, the following terms have the following meanings:

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, training pants, diaper holders and liners, sanitary napkins and the like.

"Diaper" refers to an absorbent article generally worn by infants and incontinent persons about the lower torso.

"Disposable" is used herein to describe articles that are generally not intended to be laundered or otherwise restored or reused (i.e., they are intended to be discarded after a single use and, preferably, to be recycled, composted or otherwise disposed of in an environmentally compatible manner).

"Comprise," "comprising," and "comprises" is an open ended term that specifies the presence of what follows e.g. a component but does not preclude the presents of other features, elements, steps or components known in the art, or disclosed herein.

The term "web material" refers to an essentially endless material in one direction, i.e. the longitudinal extension, or the length, or the x-direction in Cartesian coordinates relative to the web material. Included in this term is an essentially unlimited sequence of pieces cut or otherwise separated from an essentially endless material. Often, though not necessarily, the web materials will have a thickness dimension (i.e. the z-direction) which is significantly smaller than the longitudinal extension (i.e. in x-direction). Often, though not necessarily, the width of web materials (the y-direction) will be significantly larger than the thickness, but less than the length. Often, though not necessarily, the thickness and the width of such materials is essentially constant along the length of the web. Such web materials may be without intending any limitation, cellulosic fiber materials, tissues, woven or non-woven materials and the like. Typically, though not necessarily, web materials are supplied in roll form, or on spools, or in a folded state in boxes. The individual deliveries may then be spliced together to form the essentially endless structure. A web material may be composed of several web materials, such as multilayer non-woven, coated tissues, non-woven/film laminates. Web materials may comprise other materials, such added binding material, particles, hydrophilizing agents and the like.

The terms "super absorbent", "super absorbent material" or "SAM", "absorbent gelling material" or "AGM", "absorbent polymer material" are used herein interchanging, and refer to partially cross-linked polymeric materials, which can absorb water whilst they are swelling to form a gel.

The present invention is a highly efficient and accurate production method for a patterned sandwich structure, wherein particulate material is sandwiched in a very well defined amount and patterned distribution between a web material.

The present invention is particularly suitable for being used in continuous production processes, wherein the particulate material is supplied in bulk form and the carrier web is an essentially endless web material, which in course of subsequent process steps may be separated into individual web pieces, and which may form a part of a manufactured article. Such a structure is particularly useful for disposable absorbent articles, such as, but not limited to, disposable baby diapers, training pants, adult incontinence article, feminine hygiene articles and the like. Such articles have very varying requirements as to the desired absorbency depending on the intended use and/or user. In such embodiments, the carrier web materials may be fluid permeable webs, such as nonwoven materials.

The particulate material may be any particulate material. When the sandwich structures are liquid absorbent structures useful for absorbent articles, the particulate material is preferably a so called super absorbent material.

Within the context of the present invention, the term sandwich structure refers to an essentially layered arrangement of a carrier material and a cover material, and the particulate material positioned there between. The carrier and cover material are typically affixed to each other. The particles may or may not be affixed to each other and/or to the carrier/cover material. If the carrier and/or cover material has a smooth surface, the particles will typically stay on this surface. Depending on the size of the particles and on the roughness of the surface or openness of the carrier/cover material, some of particulate material may penetrate into these materials.

Typically, though not necessarily, the carrier and/or cover material will be a web material, which includes cut pieces of such a web material. The carrier and the cover material may be of the same material type, or may be different. The carrier and cover material may also be unitary, such as when a lateral side portion of the carrier material is folded over a central portion.

Figure 3B:
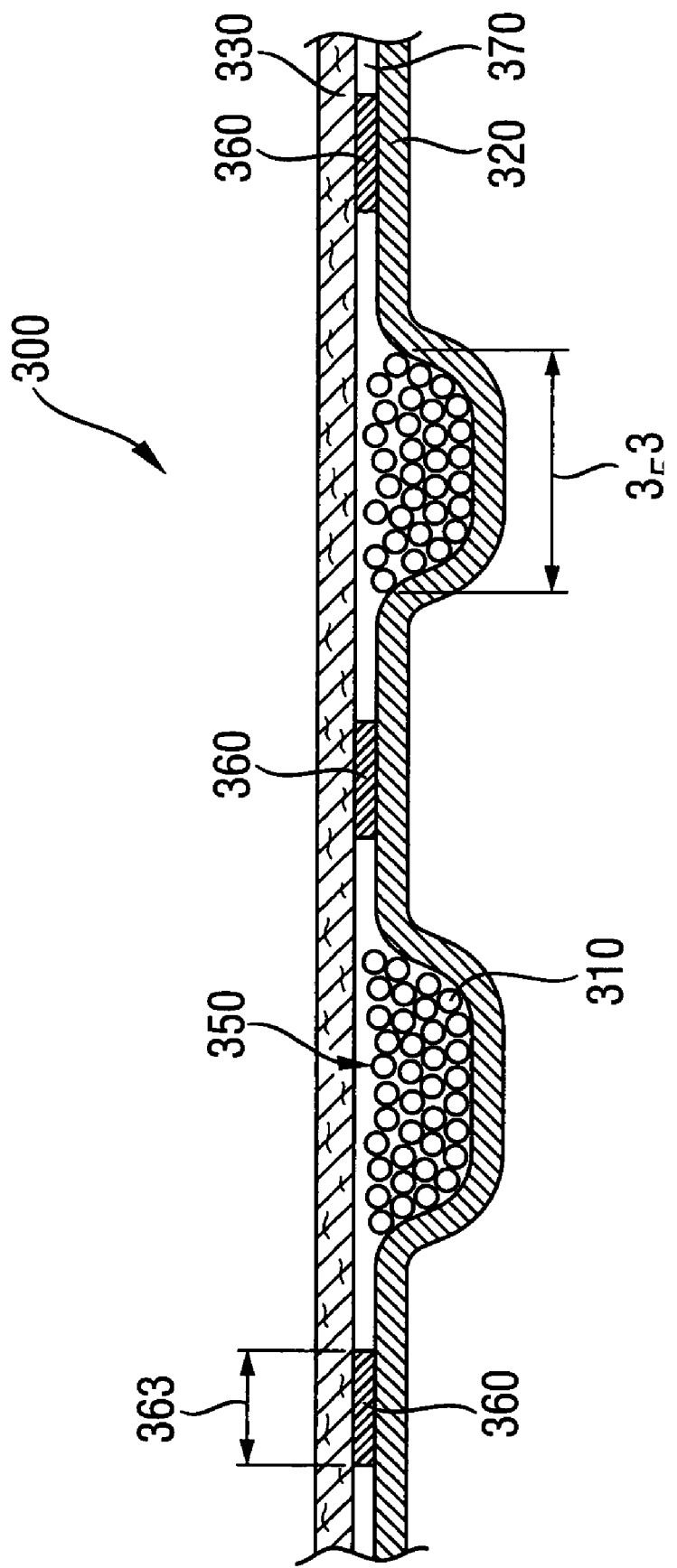
FIG. 3B is a cross-sectional view of the sandwich pattern of FIG. 3A.

A pattern of particulate material is considered to comprise a plurality of particle clusters, each comprising a plurality of particles (refer to FIG. 3). A particle cluster may be present in a sandwich structure after this has been produced. A particle cluster may also appear in course of the production process, such as when pre-metering the particulate material and pre-forming the pattern. A particle cluster in the sandwich structure may also comprise particles from different pre-formed cluster, or only a part of a pre-formed cluster. Preferably, particle cluster as created during the manufacturing process are transferred to the sandwich structure without changing shape or form.

Such a particle cluster may comprise as few as about 10 particles, but may also be up to several hundred or even several thousands of particles. The particles may be arranged essentially in a "monolayer" structure, or multi-layer structures of essentially constant thickness, or may have varying thickness. This thickness may be expressed in terms of number of overlaying particle layers, or may be expressed by local or an averaged basis weight, referring to the weight of particles for a given unit area. The skilled person will readily realize, that even a "local" basis weight will need a certain amount of averaging. However, when the basis weight in a given region is by design not constant over this region, such as may be with an increase towards the centre of the region in case of a heap or pile of granular material, the basis weight distribution may be approximated by a smoothed curve when following a cross-sectional view through this heap. Alternatively, the basis weight of a region may be designed to be constant throughout the region, such that an average basis weight for this region can be determined, optionally together with certain variability thereof. The basis weight of the neighboring regions can be the same, but are not required to be so.

A plurality of clusters is forming a primary pattern wherein the clusters are spaced apart in any geometric way. Such a pattern may comprise as few as two clusters, but will typically comprise more than ten clusters. Often, it will comprise less than 1000 clusters. Any plurality of cluster may form regular or irregular sub-patterns of the primary pattern. The clusters may be discrete or disconnected regions, such that each of these regions is essentially circumscribed by a region which is essentially free of particles.

Typically, the particles are essentially arranged to be in direct contact with each other, i.e. each particle will be in contact with at least one other particle. It may, however, also be the case, that they do not contact each other. Then however, the distance between neighboring particles within a cluster will generally be less than the distance of neighboring particle clusters within the primary or sub-pattern. (FIG. 3A, B)

Whilst the patterns are formed in an essentially continuous arrangement, there will be a certain repetition of the pattern, which will allow the same pattern to repeat in subsequent articles. Thus, the term "macro-pattern" refers to such a repeating pattern each of which may form an element of such an article.

In addition to the geometric arrangement of the particulate material in the cluster, the amount is often critical for a specific application. Henceforth, an accurate metering of the material is essential, in particular when the amount is not the same for each of the individual cluster.

Generally, the sandwich structures will need to satisfy a set of requirements as defined by the intended use. Though not to be considered limiting, a typical set of such requirements may be:
the amount and distribution of the particulate material, including the sharp definition of the pattern;
the size and shape of the sandwich structure;
the mechanical properties of the sandwich structure both with regard to allow adequate manufacturing and packaging, but also with regard to the intended use: strength, bendability, softness so as to not negatively impact comfort during use;
bonding of the elements of the sandwich structure;
the immobilization of the particulate material within the sandwich structure, both in the dry state as well as in the wet state;
variability of any of the requirements, over the length of the essentially endless sandwich structure or between pieces as being cut off an essentially endless structure.

A process for manufacturing such sandwich structures should not only satisfy the product design and quality criteria, but further be an effective and efficient method. Typically, such a process shall be capable of producing continuously at high production speed, which may require web material speeds of more than 0.5 m/sec or even more than 10 m/sec. The process should also be very flexible so as to allow for rapid changes of the product design such as from one size to another. The process as well as the equipment shall be robust so as to minimize production downtime for repair.

The present invention is providing a process satisfying all the above requirements. This is achieved by providing a manufacturing method (refer to FIG. 4) comprising the steps of
creating a pre-metered amount of particulate material in a predetermined pattern by using a pattern forming means or transfer device,
depositing the particulate material in a pattern of particle cluster on a carrier material, covering the pattern on this carrier material by a cover material, and bonding the carrier and cover web material to form the sandwich structure, thereby immobilizing the pattern.

Even further, it is important that all process steps as well as the corresponding design parameter of the equipment are precisely adapted to each other.

Without wishing to limit the present invention, the following exemplary description focuses on the manufacturing of absorbent structures as may be suitably employed in absorbent cores for disposable absorbent articles, such as baby diapers, training pants, adult incontinence products or feminine hygiene pads.

An exemplary absorbent structure is depicted in FIGS. 1 and 2. FIG. 1 is a plan view of a diaper 20 as a preferred embodiment of an absorbent article according to the present invention. The diaper is shown in its flat out, uncontracted state (i.e., without elastic induced contraction). Portions of the structure are cut away to more clearly show the underlying structure of the diaper 20. The portion of the diaper 20 that contacts a wearer is facing the viewer. The chassis 22 of the diaper 20 in FIG. 1 comprises the main body of the diaper 20. The chassis 22 comprises an outer covering including a liquid pervious topsheet 24 and/or a liquid impervious backsheet 26. The chassis may include a portion of an absorbent core 28 encased between the topsheet 24 and the backsheet 26. The chassis may also include most or all of the absorbent core 28 encased between the topsheet 24 and the backsheet 26. The chassis preferably further includes side panels 30, elasticized leg cuffs 32, and elastic waist feature 34, the leg cuffs 32 and the elastic waist feature each typically comprise elastic members 33. One end portion of the diaper 20 is configured as a first waist region 36 of the diaper 20. The opposite end portion is configured as a second waist region 38 of the diaper 20. An intermediate portion of the diaper 20 is configured as a crotch region 37, which extends longitudinally between the first and second waist regions 36 and 38. The waist regions 36 and 38 may include elastic elements such that they gather about the waist of the wearer to provide improved fit and containment (elastic waist feature 34). The crotch region 37 is that portion of the diaper 20 which, when the diaper 20 is worn, is generally positioned between the wearer's legs. The diaper 20 is depicted with its longitudinal axis 100 and its transverse axis 110. The periphery of the diaper 20 is defined by the outer edges of the diaper 20 in which the longitudinal edges 44 run generally parallel to the longitudinal axis 100 of the diaper 20 and the end edges 46 run between the longitudinal edges 44 generally parallel to the transverse axis 110 of the diaper 20. The chassis also comprises a fastening system, which may include at least one fastening member 40 and at least one landing zone 42.

For unitary absorbent articles, the chassis 22 comprises the main structure of the diaper with other features added to form the composite diaper structure. While the topsheet 24, the backsheet 26, and the absorbent core 28 may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 24 in FIGS. 1 and 2 may be fully or partially elasticized or may be foreshortened to provide a void space between the topsheet 24 and the absorbent core 28. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The absorbent core 28 in FIG. 1 generally is disposed between the topsheet 24 and the backsheet 26. In addition to the absorbent sandwich structure as described herein below, the absorbent core 28 may comprise any absorbent material that is generally compressible, conformable, non-irritating to the wearer's skin, and capable of absorbing and retaining liquids such as urine and other certain body exudates. The absorbent core 28 may comprise a wide variety of liquid-absorbent materials commonly used in disposable diapers and other absorbent articles such as comminuted wood pulp, which is generally referred to as air felt. Examples of other suitable absorbent materials include creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. The absorbent core 28 may comprise a liquid storage region 60, and other liquid handling elements 50, such as acquisition layers 52 and/or distribution layers 54. The absorbent core 28 may further comprise minor amounts (typically less than 10%) of non-liquid absorbent materials, such as adhesives, waxes, oils and the like.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

The backsheet 26 may be joined with the topsheet 24. The backsheet 26 prevents the exudates absorbed by the absorbent core 28 and contained within the article 20 from soiling other external articles that may contact the diaper 20, such as bed sheets and undergarments. In preferred embodiments, the backsheet 26 is substantially impervious to liquids (e.g., urine) and comprises a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E.I. DuPont. Other breathable backsheets including nonwoven webs and apertured formed films are described in U.S. Pat. No. 5,571,096 issued to Dobrin et al. on Nov. 5, 1996.

The diaper 20 may also include such other features as are known in the art including front and rear ear panels, waist cap features, elastics and the like to provide better fit, containment and aesthetic characteristics. Such additional features are well known in the art and are e.g. described in U.S. Pat. No. 3,860,003 and U.S. Pat. No. 5,151,092.

In order to keep the diaper 20 in place about the wearer, preferably at least a portion of the first waist region 36 is attached by the fastening member 42 to at least a portion of the second waist region 38, preferably to form leg opening(s) and an article waist. When fastened, the fastening system carries a tensile load around the article waist. The fastening system is designed to allow an article user to hold one element of the fastening system such as the fastening member 42, and connect the first waist region 36 to the second waist region 38 in at least two places. This is achieved through manipulation of bond strengths between the fastening device elements. Diaper 20 according to the present invention may be provided with a re-closable fastening system or may alternatively be provided in the form of pant-type diapers.

The embodiments of absorbent structures according to the present invention comprise a laminate structure, generally also referred to as a "sandwich" structure. This refers to a design with two essentially flat outer layers, which are web materials or cut pieces of such web materials, as may be core web materials such as tissues, woven or nonwoven materials made from hydrophilized polymeric materials and the like. One preferred material is a so called SMS material, comprising a spunbonded, a melt-blown and a further spunbonded layer. Highly preferred are permanently hydrophilic non-wovens, and in particular nonwovens with durably hydrophilic coatings. An alternative preferred material comprises a SMMS-structure.

The top layer 56 and the bottom layer 58 may be provided from two or more separate sheets of materials or they may be alternatively provided from a unitary sheet of material. Such a unitary sheet of material may be wrapped around the storage layer 60 e.g. in a C-fold.

Preferred non-woven materials are provided from synthetic fibers, such as PE, PET and most preferably PP. As the polymers used for nonwoven production are inherently hydrophobic, they are preferably coated with hydrophilic coatings. A preferred way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven as described in co-pending European patent application EP-A-1403419.

The storage layer 60 is positioned between the two layers of web material and comprises a particulate material, in particular the above mentioned superabsorbent materials. Typically, these are in irregularly shaped or spherical granules, which can swell upon contact with liquids, such as urine. Whilst this material may be in various shapes or forms, such as granular, spherical, flakes, fibrous, it will often consist of irregularly shaped particles, having a mean particle size of from 10 μm to 1000 μm, preferably with less than 5% by weight having a particle size of 5 μm, and preferably with less than 5% by weight having a particle size of more than 1200 μm.

It has been found beneficial to use a particulate absorbent polymer material for absorbent cores made in the present invention. Without wishing to be bound by theory it is believed that such material, even in the swollen state, i.e. when liquid has been absorbed, does not substantially obstruct the liquid flow throughout the material, especially when the permeability as expressed by the saline flow conductivity of the absorbent polymer material is greater than 10, 20, 30 or 40 SFC-units, where 1 SFC unit is $1 \times 10^{-7}$ (cm$^3$×s)/g. Saline flow conductivity is a parameter well recognized in the art and is to be measured in accordance with the test disclosed in EP 752 892 B (Goldman et al; P&G).

When employing such sandwich structures, there are a number of partly contradicting requirements, which these structures have to satisfy for an acceptable performance.

Thus, the particulate material is preferably immobilized. This refers to maintaining the arrangement of these particles in the structure during production as well as during use. In modern articles, the absorbency requirements in different parts of the article can be very different, such that for example more absorbency and hence absorbent material may be required in the proximity of the loading point than further away. Once the product design criteria have defined the absorbency distribution profile, this should be produced and maintained throughout the use cycle of the article, and in particular during use.

Further, the particulate material should be enabled to swell unrestrictedly. Even modern absorbent material such as described hereinabove exhibit absorbency properties depending to a certain extent on the pressure exerted on them. This pressure may be a regular use-pressure, such as when the baby as a user sits on the article. However, such a pressure may be created in sandwich structures, when, for example, the outer web material layers 56 and 58 are tightly bonded to each other in a way which does not allow expansion, thusly reducing the absorbency properties of the structure.

A further important requirement relates to the distribution of liquid throughout the structure, both longitudinally (length wise or x-directionally) and laterally (cross- or y-directionally), but also along the thickness or caliper (or z-direction) of the structure. Considering a typical baby diaper design, the overall design requirement for an absorbent structure can generally follow the description of EP-1447066 and may be as follows:

A super absorbent particulate material shall be sandwiched between non-woven web material.

The particulate material has a typical median particle size of about 400 μm, and may be a commercially available material. The non-web material may be a conventional hydrophilized SMS polypropylene web of 20 g/m$^2$ basis weight or less. The particulate material shall be deposited in a pattern of isolated "cluster" 350. The cluster (see FIG. 3A, B) shall have a uniform extension 353 in xy-direction of about 5 mm, and a distance 355 of about 10 mm. Between respective clusters, an essentially particle freed bonding zone 360 shall have a circular extension 363 of at least 3 mm. Neighboring clusters shall not be separated by a continuous bonding line or region.

The amount of particulate material in the individual clusters may vary from as much as about 0.25 g per cluster of about 15 mm diameter (which corresponds to an average basis weight of 1500 g/m$^2$ within a cluster) or as little as 1% of this value.

The particulate material is typically supplied to the process from a particle storage system, and generally will be supplied in bulk form. Bulk refers to the fact, that the multitude of particles may be described by properties and parameters relating to an individual particle, such as composition, size, shape, particle density, and so on, but also by properties and parameters relating to a multitude of such particles, such as bulk density, particle size distribution, or bulk flow properties.

Current particle deposition systems as described in the background section hereinabove are generally very speed dependent, and either create unacceptable losses or variability with regard to positioning and applied weights when being run at high speeds. The overall process comprises two sub-process sections, first the pre-metering and pattern formation, and second the sandwiching of the pattern of the particulate material between carrier and cover material.

A schematic representation of the process can be seen in FIG. 4, showing a particulate material supply 410, supplies 420 and 430 for carrier material 320 and cover material 330 respectively, a carrier support means 470, and the optional element of a particle transfer devices 440. Also shown is the resulting sandwich structure 300 with the particulate material 310 between carrier material 320 and cover material 330.

The particulate material is generally supplied to the process from a particle storage system, and generally will be supplied in bulk form. Bulk refers to the fact, that the multitude of particles may be described by properties and parameters relating to an individual particle, such as composition, size, shape, particle density, and so on, but also by properties and parameters relating to a multitude of such particles, such as bulk density, particle size distribution, or flow properties. The particulate material is deposited on a moving surface of a web material. Thusly, the process may exemplary be described to position particles from a bulk storage system in a regular pattern onto a web material.

Such processes require not only an accurate positioning of the particulate material, but should be compatible with high of even very high "converting" speeds, which correspond within the current context generally to the speed of the moving surface.

Many current particle deposition systems as described in the background section hereinabove are generally very speed dependent, and either create unacceptable losses or variability with regard to positioning and applied weights when being run at such speeds.

Co-pending EP-Patent application (attorney docket reference CM2877FQ), which is incorporated herein by reference provides a solution for the aforementioned difficulties by providing a method for indirectly applying absorbent gelling material granules onto a carrier layer for use in an absorbent article, particularly a diaper, wherein particulate granules are taken up by a transfer device from a bulk storage. Referring to FIG. 4, the transfer device 440 has recesses 452 on the surface, wherein the number, size and position thereof determine the amount and pattern of superabsorbent particles 310 taken up by the transfer device 440. The transfer device 440 is moveable from a loading position 442 adjacent to the bulk storage 410 to a discharging position 448 at which the carrier layer 320 is adjacent to the transfer device. The transfer device further has a means 444 for retaining the superabsorbent particles inside its recesses during movement of the transfer device 440 to the discharging position 448, and a means 446 for expelling the particles onto the carrier layer at the discharging meeting position 448. Preferably, these means are vacuum and blow off air, respectively.

In order to maintain the pattern of particular material, indentations 328 are formed in the carrier material 320. Essentially all of the particulate material as being expelled from one of the recesses 452 of the transfer device 440 is transferred into a corresponding indentation 328 as being formed in the carrier material, thusly forming a cluster of the sandwich pattern.

Figure 4B:
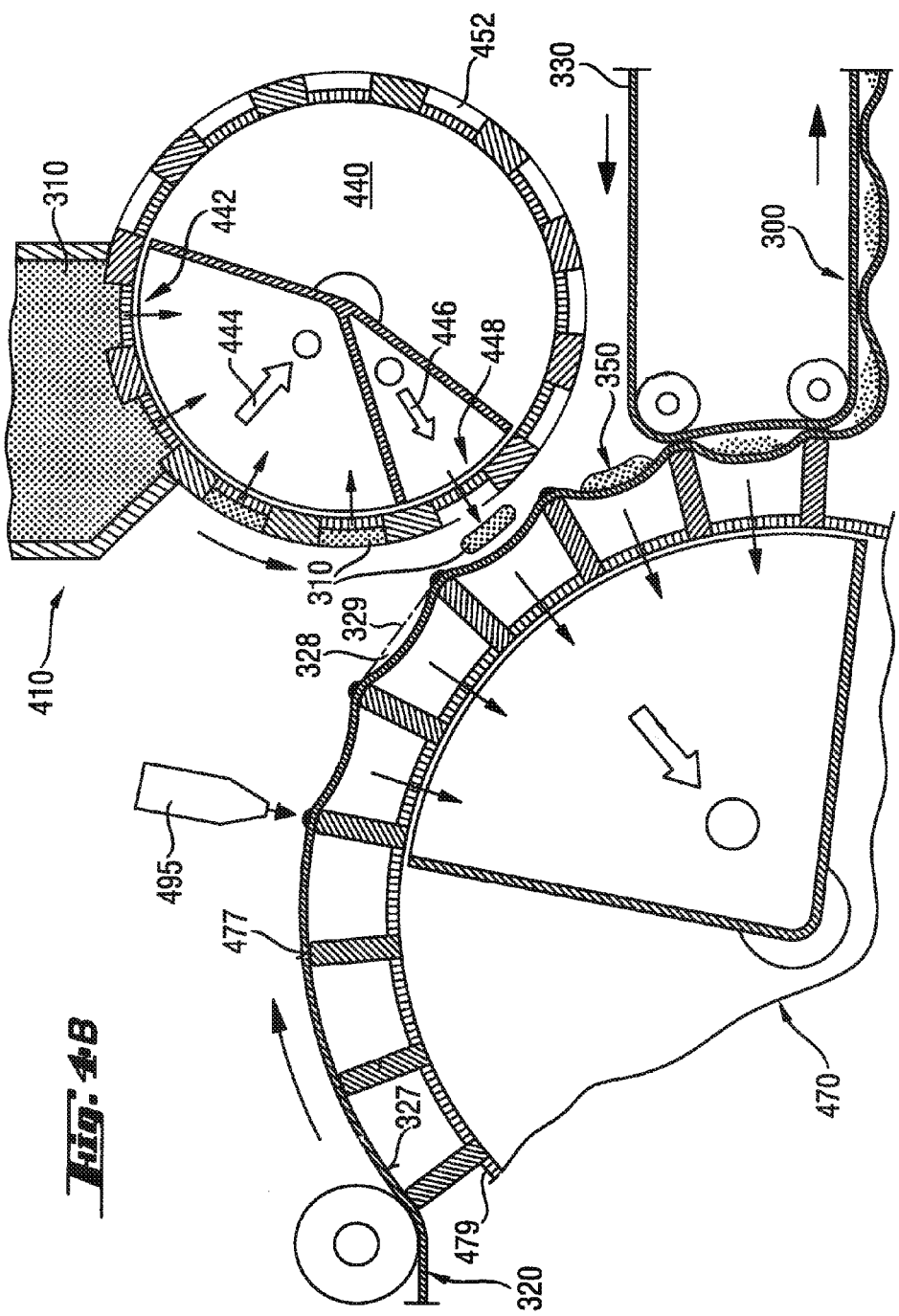
FIG. 4B is a schematic enlarged sectional view of a part of the equipment for the process as shown in FIG. 4A.

Whilst particular process and equipment settings will be required to perform the essentially complete transfer from the recesses to the carrier, the formation of the indentations greatly enhances the quality of this transfer. The indentations 328 are formed by placing the carrier material 320 on a carrier material support means 470, which has an essentially endless surface, and may be formed by a rotating drum or an endless transport belt system. The carrier material support means has a surface structure forming a particular support pattern for the carrier material (refer to FIG. 6A). Apart from the regions which are supported by the support pattern of the support structure, the carrier material is essentially unsupported, such that upon a drawing force, it may deform or bulge, forming a pocket (FIG. 4B). Such a drawing force may be a vacuum suction, such as may be applied in the support drum or in a vacuum box arranged on the side of the surface structure which is opposite to the receiving side of the carrier material, and onto which the particulate material will be deposited.

The process further comprises the steps of combining the carrier material with the particulate material thereon with a cover material 330, and of bonding the carrier and cover material by a fixation means 495, such as a spray adhesive.

The deformation of the carrier web material as well as particular aspects of the surface pattern can be found in co-filed patent application (attorney docket reference CM2988FQ), and all of the disclosure thereof is expressly incorporated herein by reference.

It is important for the present invention, that the particle pattern as formed in the recesses is precisely transferred onto the carrier web material, respectively into the pockets formed in this carrier web material. This transfer becomes increasingly more difficult to control the higher the production speed is, even if the particle transfer device and the carrier web material move at "match speed" (i.e. the surfaces have essentially the same speed relative to a fixed frame).

This is due to conflicting effects of centrifugal forces, gravity, drag forces (e.g. of moving particles in a fluid like air) in particular when a cluster of particles is moving. Further, when particles hit the surface of the carrier web material or other particles already deposited there, these may be deflected and bounce away again or bounce away other particles ("rebound" effect).

The general tendency will be that the higher the production speed becomes, the more the particles will scatter, i.e. when a cluster of particles is expelled from the recesses 452 of the transfer device 470, the particles of a cluster will have the tendency to not stay together. This may lead to less sharp definition of the pattern, and particles may land in regions which should be particle free, or even in neighboring indentations.

Whilst the formation of the pockets in the carrier web material provides an improvement in this area, focus has further to be put on the equipment design and in particular on the control of air flows.

Once the particulate material is deposited in the indentations or pockets, these may be filled partly or completely by the particles, or these may be over-filled, such as by forming a "heap". In any of these cases, it is important that at least a part of the carrier material surface is essentially free of particulate material to provide a bonding region, which is essentially free of particulate material. Typically, this area will correspond to the carrier support pattern, but may be only a part thereof or often will be larger than this, including areas surrounding the carrier support area.

The formation of the sandwich structure is completed by covering the patterned particulate material in the pockets with a cover material and fixing the two materials to each other, such as by applying adhesive material at least to the bonding region of the carrier material or to the corresponding area of the cover material.

Whilst the above description will enable a skilled person to adequately design an equipment and execute such a process, the following will describe a further aspect of the present invention, namely a method how to very rapidly arrive at the equipment design and process parameter, in particular as a reaction to a change in the requirements for the sandwich structure.

To this end, the present invention uses computerized virtual simulation tools. Such tools have become increasingly user friendly whilst at the same time also the computers have become more suitable to handle complex mathematical simulation models. Yet, the selection and combination of right tools and applying these to the right problems has hitherto not been used for addressing the formation of varying patterned sandwich structures at increased production speed.

Generally, there is a plethora of approaches to mathematical/physical simulations available, such as without limitation:
- basic Finite element analysis, allowing three dimensional (3D) geometric simulation;
- upon addition of time as a variable, movement maybe dynamically simulated;
- adding mass to the geometric 3D simulation allows simulation of matter and surfaces.
- adding forces to the simulation will lead to kinetic simulation;
- adding energy (potential) will allow interaction of forces and energy transformation, in particular also fluid dynamics.

In addition, particular specific elements may be added to each and any of the above simulations. Such elements may be temperatures, pressures, reactivity of chemical matter, etc.

The overall approach for all of these simulations is to build a representative physical and mathematical model of the real process, i.e. setting up mathematical equations relating to physical structures or processes. For all these equations, suitable boundary conditions have to be provided so as to allow solving the set of equations to give a solution for this set of conditions.

These general teachings will now be further explained by using the manufacturing process of a disposable absorbent article, such as a diaper as described in the above.

The models can build on conventional modeling tools for particular simulations. Thus in general terms, the virtual simulation can be described to be a method for determining the equipment design and process parameter for a process for selectively positioning particulate material onto a moving surface, by 1) providing a set of physical equations forming a physical model, the set of physical equations being connected by interaction boundary conditions, optionally comprising sub-models connected by sub-model connectivity boundary conditions;
2) selecting a set of fixed boundary conditions, comprising the overall equipment set-up, overall process requirements, and a set of (initial) operating conditions (fixed model input);
3) providing a set of predetermined model targets
4) selecting a set of variable boundary conditions, which may vary throughout one simulation (variable model input);
5) performing calculus operations on the physical equations by using the fixed and variable model input;
6) transforming the calculus results into a model output, which is readable to a human analyst directly or preferably by a means of a computing device;
7) comparing the model output to predetermined model targets and determining the deviation there between, preferably by using computer;
8) modifying the set of variable boundary conditions, preferably by using computational equations for minimizing the deviation between the model output to predetermined model targets;
9) reiterating steps 4) to 8) until a preset exit criterion is met; the exit criterion preferably being a certain number of iterations, more preferably being a preset exit deviation between the model outputs and the predetermined model targets.

Preferably, the simulation will be performed by using a computer system, such as may include a processing unit connected to a user interface, which may include a display terminal, a keyboard, a pointing device, such as a mouse, and the like. The processing unit may include a central processing unit, a memory, and stored instructions, which implement a method to assist in determining the process and design parameter according to the present invention. The stored instructions may be stored within the processing unit in the memory, or in any non-volatile storage such as magnetic or optical media, EPROM, EEPROM, or the like. Alternatively, instructions may be loaded from removal media, such as a removal disk, sometimes called a floppy disk, optical media, or the like. In a preferred embodiment, the system includes a general purpose computer program to implement the functions described herein. Optionally, the computer set up may also include a printer or a network connection for accessing a local server, an intranet, and the Internet.

In particular, the present approach utilizes virtual simulation and calculation tools.

The various equipment elements can be designed by using static, dynamic, or kinematic models. Typical tools for such calculations are MSC.visualNASTRAN 4D™ or MSC.DynamicDesigner™, both available from available from MSC-.Software Corporation, Santa Ana, Calif., USA When calculating the behavior of and in particular the interactions between particles in a bulk flow, a typical tool for such calculation can be found in "Particle Flow Code" in 2 or 3 dimensions (PFC2D/PFC3D), such as available from HCItasca via Itasca Consultants; Gelsenkirchen, Germany.

An important simulation aspect deals with fluid flow patterns, which can be addressed by computational fluid dynamics (CFD) solver, such as FLUENT, FloWizard, FIDAP; POLYFLOW, as available from Fluent Incorporated, Lebanon, N.H., USA.

A further important simulation tool deals with deformation of materials, such as web materials, under the impact of external forces, such as induced by the air flow through the material. A suitable tool has been found in ANSYS Mechanical™, as available form ANSYS Inc., Canonsburg, Pa., USA.

Having selected the suitable tools, a first set of boundary conditions will be set. This relates to the "fixed" conditions, which will essentially remain unchanged during the simulation, and relates to the definition of the materials, here of the employed particulate materials, or web materials. In the present case, other general boundary conditions are the operation under "ambient" conditions, in particular that the process will be operated at or around normal air conditions, which may, however, be stabilized, such as to 20° C., 50% relative humidity. "Ambient" pressure conditions may include, that certain parts of the equipment may be subjected to a certain pressure change (such as vacuum) so as to induce air flow.

Similarly fixed boundary conditions related to the key equipment elements, for the case of producing the sandwich structure for disposable diapers, the particulate material will be delivered in bulk to a hopper system, metered via a pre-metering and transfer drum and transferred to a web material as carrier, before the sandwich structure is covered and affixed.

Whilst these boundary conditions will not be changed for a given simulation, these may be—and typically will be—changed so as to assess e.g. robustness of the system.

In a further step, the target parameter will be set. In the present case these may be the design parameter for the absorbent sandwich structure, such as the geometry of patterns, the amount, basis weights and distribution of materials and so on. An important target parameter for the simulation is the presetting of the process speed. These targets are typically defined for the total process, although certain aspects may relate to one or more of the sub-process steps only.

The model calculation may be run as one complete iteration, or there may be iterations of sub-sets of the models. In case of using sub-models, these may be connected automatically, such that one modeling program transmits the sub-model boundary conditions to a connected other sub-model. Alternatively, the sub-models may be executed "step-by-step", i.e. each simulation step may be done independently from the other, and the boundary conditions from one step will be inputted into the next simulation.

For each of the sub-systems, a set of input parameter will be defined as well as a set of result parameter.

In a first simulation step, the transfer of the particulate material to the pattern forming device is considered.

Starting point is a "translation" of the target design pattern in the sandwich to a distribution of cluster sizes, basis weights and to an initial design of the recesses.

The results of such a simulation step will be an initial design (depth, shape . . . ) of the recesses of the transfer drum will be designed. The general size of the recesses is determined to be 2-25 mm in diameter, and the depth will vary from about 0.5 mm to about 10 mm. A recess which corresponds to a cluster which has less particulate material than required for a monolayer of particles will be made smaller in diameter so as to enable accurate filling.

Upon consideration of particle to particle forces and pressures, the filling of the recesses may be investigated, resulting in a detailed design of the recesses, including the sloping of the side walls, edge curvatures, relative positioning of the particle delivering device (e.g. hopper) to the recesses, use of and if used, the distance of scraping means (e.g. a doctor blade). Also, the application of vacuum through an air permeable bottom of the recesses will be evaluated.

The subsequent simulation step is the movement of the particle filled recesses from the particle receiving region to the particle expelling region. When considering the preferred embodiment of a steadily rotating cylindrical transfer drum, there needs to be a balance of the centrifugal forces and the withholding forces, such as air flow forces as caused by a vacuum within the transfer drum.

A key simulation step relates to the particle transfer from the transfer or printing roll onto the carrier web material. This has a number of interacting elements, namely expelling the particles out of the recesses; movement of the particles towards the carrier; Interacting with the air flow as well as air flow disturbances as induced by the particle cluster itself; calculations of particle and particle cluster trajectories. Ideally, the relative positioning of the particles in a cluster does not change, i.e. a cluster should be transferred "as is" from the transfer drum to the carrier material. The air flow stream simulation in the region of the particle trajectories needs to further take into account secondary air flow streams.

The results of this simulation will be the accurate positioning of the transfer device relative to the carrier web support means, the accurate point of expelling the particles and respective conditions; and the identification of secondary air flows, such as disturbances e.g. from adhesive sprays;

In order to design the pockets of the carrier material, two important aspects have to be simulated: First, the pattern of the indentations shall reflect the pattern as desired for the final sandwich structure. Second, the formation of the indentations needs to consider the deformation properties of the carrier material. The non-isotropic stress strain behavior of the web may result in an angled arrangement of the pattern.

Additional simulation tools may be applied to other process aspects, and may then be connected to respective simulation steps, with which they may interfere. An example for such a process step is the application of a spray adhesive to the web carrier material prior and/or after the deposition of the particles, which will interfere with the air flow around the particles. A further example may be design structural design aspects for all of the elements.

Having thusly defined the iteration procedure, the simulation steps will start, and will be iterated until the preset targets are reached, or any other stop criteria is met (e.g. number of automatic iterations).

A simulation has been carried out for the production of an absorbent sandwich structure as described herein above at a production speed of 8 m/sec. The simulation results allowed designing the improved process in particular for:

The filling of the recesses by improving the shape of the recesses;

Adjustment of the vacuum for holding the particles in the recesses;

Calculation of appropriate "blow off air" for expelling the particles;

Evaluation of the complete air flow pattern impacting on the trajectories of the particles after being expelled from the transfer device;

Deformation of the carrier material by applying vacuum suction to form the indentations;

Determining the landing of the particles respectively particle cluster on the carrier material.

These simulations have been translated into a full scale production unit designed by using the results, and production trials confirmed the possibility of using the simulation results for preparing a sandwiched structure with a very well defined particulate pattern at high production speed of at least 4.2 m/sec.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention.

Each parameter for which a value is defined herein is a technical parameter, which in the context of the present invention is not to be understood literal. Hence, all embodiments having parameters functionally equivalent to the parameters stated herein are intended to be covered by the scope of the invention, e.g. a length of "10 mm" has to be understood as meaning "about 10 mm".

What is claimed is:

1. A method for determining the equipment design and process parameters for a process for selectively positioning particulate material onto a surface of a web material while said web material is moving at a production speed, the method comprising the steps of:
   a.) providing a set of physical equations forming a physical model, wherein the set of physical equations is connected by interaction boundary conditions;
   b.) selecting a set of fixed boundary conditions;
   c.) providing a set of predetermined model targets;
   d.) selecting a set of variable boundary conditions;
   e.) performing calculus operations on the physical equations by using the initial operating conditions and variable boundary conditions, wherein the calculations are performed by employing a computer device;
   f.) transforming the calculus results into a model output which is readable to a human analyst directly or by a means of a computing device;
   g.) comparing the model output to predetermined model targets and determining the deviation therebetween;
   h.) modifying the set of variable boundary conditions using computational equations for minimizing the deviation between the model output to predetermined model targets; and
   i.) repeating steps d.) through h.) until a preset exit criterion is met;
   wherein the set of fixed boundary conditions are selected from the group consisting of: transferring a cluster of particulate material into a receiving region of a transfer device, whereby the receiving region of the transfer device defines a particulate cluster pattern; holding the cluster of particulate material on the transfer device by applying vacuum to the transfer device; moving the receiving region of the transfer device to a discharging region of the transfer device; guiding the web material over a carrier support structure; deforming the web material by the carrier support structure such that an indentation is formed in the unsupported regions, thereby forming a pattern in the indentation corresponding to the particulate cluster pattern; forming indentations in the web material on the carrier support structure by applying vacuum to the web material; expelling the cluster of particulate material from the transfer device toward the indentation in the web material; depositing the cluster of expelled particulate material on the deformed web material; applying a cover material to the carrier material and the cluster of particulate material, thereby forming a sandwich structure; and bonding the web material and the cover material to each other;
   wherein the model targets are selected from the group consisting of: a target cluster design pattern; the quantity of particulate material in the cluster; the basis weight of the cluster of particulate material; a distribution of the particulate material clusters on the web material; and the production speed; and
   wherein the variable boundary conditions are selected from the group consisting of: a shape of the particulate cluster pattern on the receiving region of the transfer drum; vacuum required in the transfer device for holding the particulate material; a pattern of air flow of the particulate material cluster as it is expelled toward the carrier material; air flow required to expel the particulate material clusters toward the web material; deformation of the web material by applying vacuum to form the indentations; and a trajectory of the particulate material cluster as the particulate material cluster is expelled toward the carrier material.

2. The method of claim 1, wherein the exit criterion is defined by a preset number of iterations.

3. The method of claim 1, wherein the exit criterion is defined by a preset exit deviation criterion between the model output and the predetermined model targets.

4. The method of claim 1, wherein the set of physical equations being connected by interaction boundary conditions includes sub-models connected by sub-model connectivity boundary conditions.

5. The method of claim 1, wherein the set of variable boundary conditions varies throughout one simulation.

6. The method of claim 1 wherein said particulate material forms a pattern of particle clusters on said web material after deposition of said particulate materials onto said moving web material.

7. The method of claim 1 comprising the step of obtaining equipment for making an absorbent article based on said equipment design.

* * * * *